(12) United States Patent
Knerr

(10) Patent No.: US 6,277,815 B1
(45) Date of Patent: Aug. 21, 2001

(54) SOLUTION FOR PERITONEAL DIALYSIS

(75) Inventor: Thomas Knerr, St. Wendel (DE)

(73) Assignee: Fresenius Medical Care Deutschland GmbH (DE)

( * ) Notice: Subject to any disclaimer, the term of this patent is extended or adjusted under 35 U.S.C. 154(b) by 0 days.

(21) Appl. No.: 09/183,225

(22) Filed: Oct. 30, 1998

(30) Foreign Application Priority Data

Oct. 31, 1997 (DE) .............................................. 197 48 290

(51) Int. Cl.$^7$ .................................................. A61K 38/00
(52) U.S. Cl. .................................. 514/2; 514/23; 514/53; 514/54; 424/676
(58) Field of Search .................................. 514/2, 23, 53, 514/54; 424/676

(56) References Cited

U.S. PATENT DOCUMENTS

| | | | |
|---|---|---|---|
| 4,630,727 | * 12/1986 | Feriani et al. | 206/221 |
| 5,071,558 | * 12/1991 | Itob | 2100/542 |
| 5,296,242 | * 3/1994 | Zander | 424/717 |
| 5,827,820 | * 10/1998 | DuMoulin et al. | 514/2 |
| 5,945,129 | * 8/1999 | Knerr et al. | 424/676 |

FOREIGN PATENT DOCUMENTS

| | | |
|---|---|---|
| 4122754 | * 1/1993 | (DE). |
| 196 54 746 | 7/1998 | (DE). |
| 076 355 | 4/1983 | (EP). |
| 08131542 | * 5/1996 | (JP). |
| 09087182 | * 3/1997 | (JP). |
| 11070166 | * 3/1999 | (JP). |
| WO 91/08008 | 6/1991 | (WO). |
| WO 93/09820 | 5/1993 | (WO). |
| 93/19792 | * 10/1993 | (WO). |
| WO 96/01118 | 1/1996 | (WO). |
| WO 97/06810 | 2/1997 | (WO). |
| 99/09953 | * 3/1999 | (WO). |

OTHER PUBLICATIONS

Comstock, T. "Renal Dialysis—Chapter 31", Applied Therapeutics—The clinical use of drugs (sixth ed.), edited by Young and Koda–Kimble, pp. 31–1 to 31–15, 1995.*

H.E. Franz, "Blood Purification Methods," published by Georg Thieme Verlag, Stuttgart, NY, 1990, pp. 479–492.

\* cited by examiner

*Primary Examiner*—Ralph Gitomer
*Assistant Examiner*—D Khare
(74) *Attorney, Agent, or Firm*—Kenyon & Kenyon

(57) ABSTRACT

A solution for peritoneal dialysis or for infusion comprises two single solutions which, after heat sterilization, are brought together and dispensed, with the first single solution containing calcium ions, additional electrolytic salts and glucose in an osmotically effective concentration and the second single solution containing bicarbonate and a weak acid with pKa<5. To provide a biocompatible solution, in particular for use as a peritoneal dialysis solution, the first single solution is acidified with a physiologically compatible acid to a pH of below 3.2. The second single solution contains bicarbonate only in a proportion which does not exceed 10 mmol/l.

13 Claims, 1 Drawing Sheet

SOLUTION FOR PERITONEAL DIALYSIS

FIELD OF THE INVENTION

The present invention relates to a solution for peritoneal dialysis or for infusion.

BACKGROUND INFORMATION

A peritoneal dialysis solution generally contains three functional constituents. First, it contains electrolytes, which in this case are calcium. sodium and magnesium salts which, as a rule, are used in chloride form. A buffer is provided as the second functional constituent. The best tolerated buffer system consists of bicarbonate that is at equilibrium with carbonate in the alkaline region and with $CO_2$, in the acid region. Substances that buffer at a pH of approximately 7, that is, at a physiological pH, could also be used as buffers. Substances which can easily be metabolized to bicarbonate inside the body. such as lactates, pyrovates or similar substances, are preferred. The third functional constituent consists of an osmotic substance. Here, glucose is frequently used, which at a relatively low concentration has a high osmolarity and is well tolerated. One reason for the frequent use of glucose is its favorable price compared to other substances that might be used as the osmotic substance.

WO 96/01118 discloses, for example, a solution for peritoneal dialysis or infusion, bicarbonate is used in physiological quantities of 20–30 mEq/l together with a weak acid in a quantity of 10–20 mEq/l. When such a peritoneal dialysis solution is used. it is necessary that the bicarbonate contained and the calcium contained be stored separately, as storing them together very easily leads to an insoluble calcium carbonate precipitation. In the acid region, this, precipitation can be avoided, as the bicarbonate continues to be at equilibrium with the carbon acid, and so with $CO_2$, so that less carbonate is present. However, this has the disadvantage that a relatively high $CO_2$ partial pressure is created. This high $CO_2$ partial pressure in turn requires a bag film with an effective $CO_2$ banier so that especially adapted bags with a relevant $CO_2$ barrier layer can be used.

In EP 0 076 355 A the bicarbonate has, for example, been replaced by lactate as the buffer to avoid problems in the handling of a solution containing bicarbonate. However, the use of lactate causes another problem during heat sterilization, as lactate and the glucose that is also present in the solution react to form acetaldehyde. Acetaldehyde, however, damages the peritoneal walls.

Furthermore, heat sterilization also causes glucose to be caramelized, isomerized or broken down into products which can continue to react irreversibly with proteins inside the body. This and other problems led in EP 0 076 355 A to the replacement of glucose, for example, by glucose polymers (such as icodextrine), peptides or proteins such as albumin. This glucose replacement, however. leads to a considerable price increase of the product. In addition, physiological reactions, such as immune reactions, were observed with the use of these substitutes. Finally, similar problems to those of glucose could also be observed with glucose polymers during heat sterilization so that different ways had to be found to avoid the glucose breakdown.

In this respect WO 93/09820 teaches on the one hand separate storage for a corresponding system and, on the other hand, short but high-temperature heating for the purpose of sterilization. In the case of separate storage. glucose is largely stored in a separate container to avoid reactions with other constituents such as lactate. According to this teaching, the glucose solution can be heated briefly and at very high temperature while the solution together with the other constituents can be subjected to the usual sterilization conditions without problems.

Another way of solving the problems described with regard to EP 0 076 355 A is described in WO 91/08008 where sterilization can be performed at very low pH values of below 3. This again leads to the problem that at these low pl I values a weak acid, such as lactic acid or its salt. the lactate, is not sufficient as a weak base for buffering to achieve a physiological pH of around 7.2 to 7.4 in a final solution.

SUMMARY OF THE INVENTION

An object of the present invention is to provide a solution for peritoneal dialysis or infusion which, on the one hand, ensures good storability and easy and safe handling and, on the other hand, good biocompatibility.

The present invention provides a solution for peritoneal dialysis or infusion comprising two single solutions which, after heat sterilization, can be brought together and dispensed. The first single solution contains calcium ions, additional electrolytic salts and glucose in an osmotically effective concentration and the second single solution contains bicarbonate and the salt of a weak acid with pKa<5. The present invention is characterized in that the first single solution is acidified with a physiologically compatible acid to a pH of below 3.2 and the second single solution has a bicarbonate content which does not exceed 10 mmol/l.

Here, a buffer from lactate and bicarbonate is provided in accordance with the present invention. Due to the bicarbonate proportion, a physiological pH of around 7.2 to 7.4 can be achieved in the final solution. It is essential that the bicarbonate content is below 10 mmol/l, since, surprisingly, as a result the $CO_2$ pressure inside the storage bag is so low that the barrier of a normal polyolefin film or of a normal PVC film is sufficient to keep the bicarbonate concentration constant. The difficult handling problems of the solution. which usually contains bicarbonate, and/or the requirements of a $CO_2$ barrier film can thus be avoided. To keep the bicarbonate content that low the main buffer comprises a salt of a physiologically weak acid, preferably lactate, whose buffer capacity is merely supported by the bicarbonate in this combined buffer. While lactate and bicarbonate can be stored in a bag chamber, glucose and the electrolytes—and together with the electrolytes the calcium ion—can be acidified and sterilized in a second chamber to a pH of below 3.2. After sterilization the contents of both chambers can be combined, mixed and dispensed to the patient.

The solution in accordance with the present invention has a compatible pH and fewer glucose breakdown products. Thus, it achieves high biocompatibility. It is particularly advantageous that, with the solution in accordance with the present invention, the pain of administration can also be avoided for dialysis patients due to a reduction of the glucose breakdown.

In accordance with a particularly advantageous embodiment the first single solution, which comprises calcium ions, additional electrolytic salts and the glucose, has a pH of 2.8 to 3.2, preferably a pH of 3. Due to the acidification of this single solution which contains the glucose, a clear reduction of the glucose breakdown is achieved during sterilization. The second single solution, which contains bicarbonate and the salt of a weak acid, should have a pH of 8 to 8.5. When mixing, the single solutions at a ratio of about 1 to 1 (by weight), a pH of 7.2 to 7.4 is achieved for the final solution.

In addition to calcium ions and glucose, the first single solution may also contain sodium ions, magnesium ions, $H^+$ excess ions and chloride ions as additional electrolytes. The second single solution may contain hydrogen carbonate ions in addition to sodium ions and lactate ions, for example pyruvate ions, α-keto glutarate ions etc.

The physiologically compatible acid of hydrochloric acid for acidification to a pH of below 3.2 is also advantageous.

A particularly compatible separation of the solution into the two single solutions is achieved as follows:

First Single Solution:

| | |
|---|---|
| Sodium [mmol/l] | 180 to 200, preferable 193 |
| Calcium [mmol/l] | 2 to 4, preferably 2.5 to 3.5 |
| Magnesium [mmol/l] | 0.8 to 1.2, preferably 1.0 |
| H + excess ions [mmol/l] | 0.9 to 1.1, preferably 1.0 |
| Chloride [mmol/l] | 197 to 210, preferably 203 |
| Glucose [mmol/l] | 100 to 500, preferably 166.5, 252 or 473 |

Second Single Solution:

| | |
|---|---|
| Sodium [mmol/l] | 70 to 80, preferably 75 |
| Lactate [mmol/l] | 65 to 75, preferably 70 |
| Hydrogen carbonate [mmol/l] | 4 to 6, preferably 5.0. |

DETAILED DESCRIPTION

Figure 1:
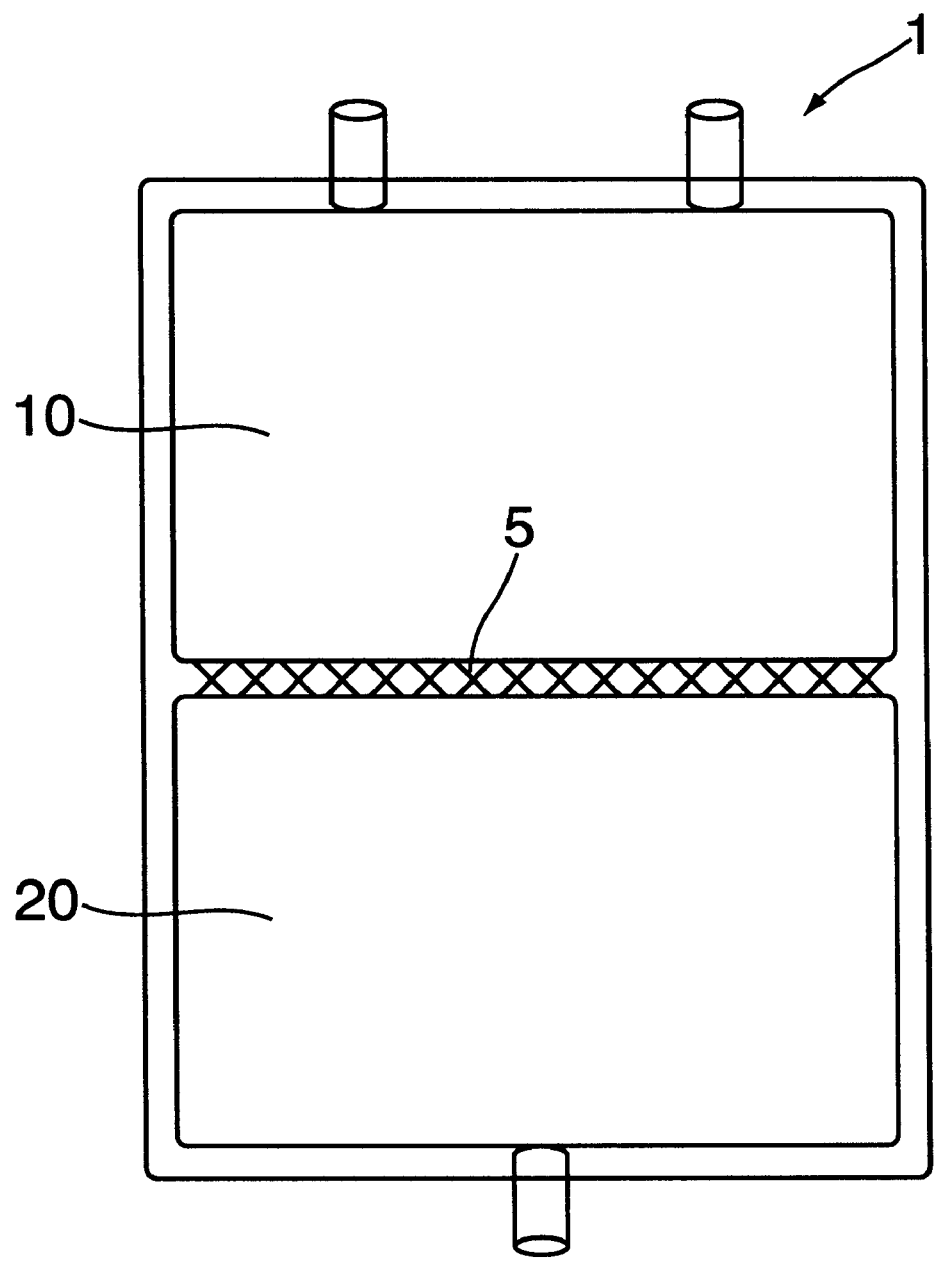
FIG. 1 shows an exemplary embodiment of the double chamber bag of the present invention for holding the two single solutions.

A particularly good handling of the two solutions of the invention is obtained by the use of a double-chamber bag, which for example may comprise ordinary polyolefin. Accordingly, as shown in FIG. 1, a plastic bag 1 comprises a first chamber 10 for the first solution and a second chamber 20 for the second solution disposed adjacent to each other with both chambers being separated from each other by a weld 5. The weld 5 is dimensioned such that it opens upon pressure to one of the fluid-filled chambers so that the contents of both chambers can be mixed together.

Double-chamber bags which were previously known possessed an injection-molded part as a separating part between the two chambers, which was opened by breaking off. As a rule, however, this opened only passageways of less than 10 mm. Since one solution had to be pressed from one chamber into the next and back again to mix the solutions, a time-consuming mixing procedure was required which reduced the acceptance of the double-chamber bag among patients. These disadvantages have been overcome with the double-chamber bag of the present invention.

In the following an example for the manufacture of a solution in accordance with the present invention is given:

To produce the first single solution, 11.279 g sodium chloride, 0.5145 g calcium chloride×2H$_2$O, 0.2033 g magnesium chloride×6H$_2$0,33 g glucose monohydrate for injection purposes and 0.130 ml 25% hydrochloric acid are brought into solution by stirring in 973 ml water for injection purposes. Any necessary correction of the pH can be performed by adding or omitting 25% hydrochloric acid or sodium hydroxide. The solution, thus set at the desired pH, is filtered through membrane prefilters and then through membrane sterile filters into a cooling tank. After a preparation inspection and release of the solution, the latter is filled into a double-chamber multilayer-film bag and closed with connectors. The dry bag is then repacked into a surrounding bag and then heat-sterilized at 121 degrees C.

For the second single solutions 15.69 g sodium lactate as a 50% solution and 0.420 g sodium hydrogen carbonate are dissolved by slow stirring in 986 ml water for injection purposes which has been cooled down to 12 to 14 degrees C. The temperature of the solution should not exceed 20 degrees C. during the preparation and storage time. Then the solution is filtered through membrane prefilters and membrane sterile filters into a cooling tank. After completion of the preparation inspection and release of the solution, the latter is filled into the double-chamber bag and closed with connectors. The dry bag is repacked into a surrounding bag. Then it is sterilized at 121 degrees C.

For use, the two single solutions are mixed at a ratio of about 1 to 1 (by weight).

What is claimed is:

1. A solution for peritoneal dialysis or infusion comprising:

a first single solution comprising calcium ions, additional electrolytic salts and glucose in an osmotically effective concentration, the first single solution being acidified with a physiologically compatible acid to a pH of below 3.2; and a second single solution comprising bicarbonate and the salt of a weak acid with a pKa<5, the bicarbonate of the second single solution not exceeding a concentration of 10 mmol/l;

wherein the first and second single solutions are brought together after heat sterilization to form a dispensable finished solution.

2. The solution as recited in claim 1 wherein the first single solution has a pH I of 2.8 to 3.2 and the second single solution has a pH of 8 to 8.5, the first and second single solutions being brought together at a ratio of about 1 to 1, by weight, so that the finished solution has a pH of approximately 7.2 to 7.4.

3. The solution as recited in claim 2 wherein the first single solution has a pH of 3.0.

4. The solution as recited in claim 1 wherein the first single solution includes sodium ions, magnesium ions, H$^+$ excess ions and chloride ions.

5. The solution as recited in claim 1 wherein the second solution contains hydrocarbonate ions and sodium salts of weak acids selected from the group consisting of pyruvate and lactate.

6. The solution as recited in claim 1 wherein the physiologically compatible acid is hydrochloric acid.

7. The solution as recited in claim 1 wherein the first single solution comprises constituents in concentrations as follows:

| | |
|---|---|
| Sodium [mmol/l] | 180 to 200 |
| Calcium [mmol/l] | 2 to 4 |
| Magnesium [mmol/l] | 0.8 to 1.2 |
| H+ excess [mmol/l] | 0.9 to 1.1 |
| Chloride [mmol/l] | 197 to 210 |
| Glucose [mmol/l] | 100 to 500. |

8. The solution as recited in claim 1 wherein the second single solution comprises the constituents in the concentrations as follows:

| | |
|---|---|
| Sodium [mmol/l] | 70 to 80 |
| Lactate [mmol/l] | 65 to 75 |
| Hydrogen carbonate [mmol/l] | 4 to 6. |

9. The solution as recited in claim 7 wherein the first single solution comprises the constituents in the concentrations as follows:

| | |
|---|---|
| Sodium [mmol/l] | 193 |
| Calcium [mmol/l] | 2.5 to 3.5 |
| Magnesium [mmol/l] | 1.0 |
| $H^+$ excess [mmol/l] | 1.0 |
| Chloride [mmol/l] | 203 |
| Glucose [mmol/l] | 166.5, 252 to 472. |

10. The solution as recited in claim 8 wherein the second single solution comprises constituents in concentrations as follows:

| | |
|---|---|
| Sodium [mmol/l] | 75 |
| Lactate [mmol/l] | 70 |
| Hydrogen carbonate [mmol/l] | 5.0. |

11. The solution as recited in claim 1 wherein the two single solutions are stored separately in a double-chamber bag before being brought together.

12. The solution of claim 5 wherein the second solution contains hydrocarbonate ions and sodium α-ketoglutarate.

13. A method of making a solution for peritoneal dialysis or infusion comprising:

a) providing a first solution comprising calcium ions, additional electrolytic salts and glucose in an osmotically effective concentration, the first single solution being acidified with a physiologically compatible acid to a pH of below 3.2;

b) providing a second solution comprising bicarbonate and the salt of a weak acid with a pKa<5, the bicarbonate of the second single solution not exceeding a concentration of 10 mmol/l;

c) heat sterilizing the first solution;

d) heat sterilizing the second solution;

e) bringing the first and second solutions together to form a finished solution.

\* \* \* \* \*